United States Patent [19]

Adam et al.

[11] Patent Number: 5,302,704
[45] Date of Patent: Apr. 12, 1994

[54] AZODYES CONTAINING A SULFOACETOACETIC ACID ANILIDE COUPLING COMPONENT

[75] Inventors: Jean-Marie Adam, Rosenau, France; Thomas Eichenberger, Basel, Switzerland

[73] Assignee: Ciba-Geigy Corporation, Ardsley, N.Y.

[21] Appl. No.: 924,140

[22] Filed: Aug. 3, 1992

[30] Foreign Application Priority Data

Aug. 8, 1991 [CH] Switzerland .................. 2344/91-1

[51] Int. Cl.$^5$ .................. C09B 29/033; C09B 29/33; D06P 1/06; C07C 309/14
[52] U.S. Cl. .................. 534/738; 534/741; 534/744; 548/180; 548/224; 548/261; 548/310.7; 549/58; 549/469; 562/44
[58] Field of Search .............. 534/845, 738, 741, 744; 548/180, 224, 261, 310.7; 549/58, 469; 562/106, 44; 564/200

[56] References Cited

U.S. PATENT DOCUMENTS

| | | | |
|---|---|---|---|
| 1,159,386 | 11/1915 | Huismann | 534/741 |
| 1,833,269 | 11/1931 | Stusser | 534/741 |
| 2,328,353 | 8/1943 | Mackenzie | 562/106 X |
| 2,657,202 | 10/1953 | Moser | 534/741 |
| 3,150,151 | 9/1964 | Urbschat et al. | 534/741 X |
| 3,274,171 | 9/1966 | Anderson et al. | 534/741 |
| 4,052,157 | 10/1977 | Fuchs et al. | 534/744 X |
| 4,234,480 | 11/1980 | Kramer | 534/741 |
| 4,399,068 | 8/1983 | Kramer | 534/744 X |
| 4,419,290 | 12/1983 | Dehnert et al. | 534/744 X |
| 4,736,021 | 4/1988 | Adam et al. | 534/741 X |
| 4,881,977 | 11/1989 | Bauer | 106/22 |
| 4,894,447 | 1/1990 | Adam | 534/741 X |

FOREIGN PATENT DOCUMENTS

| | | |
|---|---|---|
| 0183151 | 6/1986 | European Pat. Off. |
| 0311949 | 4/1989 | European Pat. Off. |
| 2294263 | 12/1975 | France |
| 2378003 | 8/1978 | France |
| 2401197 | 3/1979 | France |

OTHER PUBLICATIONS

Venkataraman, The Chemistry of Synthetic Dyes, 1978 vol. VIII pp. 312–315.
O'Connor, "Tautomerism in Phenylhydrazones", J. Am. Chem. Soc., 26, 4375–4380 (1961).
Yao et al, "Azo-Hydrazone Conversion. I. The Japp-Klingemann Reaction", J. Am. Chem. Soc., 84, 3514–3517 (1962).
March, Advanced Organic Chemistry, Third Ed., 1985, 532–533.

Primary Examiner—Mary C. Lee
Assistant Examiner—Fiona T. Powers
Attorney, Agent, or Firm—Kevin T. Mansfield; Edward McC. Roberts

[57] ABSTRACT

Dyes of formula

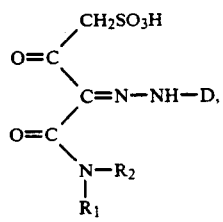

(1)

wherein D is the radical of a diazo component of the benzene or naphthalene series or of the heterocyclic series, $R_1$ is hydrogen or $C_1$–$C_4$alkyl and $R_2$ is phenyl or substituted phenyl, give dyeings of good fastness properties on nitrogen-containing or hydroxyl group containing fibre materials.

6 Claims, No Drawings

AZODYES CONTAINING A SULFOACETOACETIC ACID ANILIDE COUPLING COMPONENT

The present invention relates to novel dyes, to their preparation and to the use thereof for dyeing and printing fibre materials, especially textile materials.

Specifically, the invention relates to dyes of formula

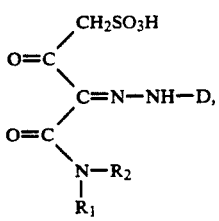

(1)

wherein D is the radical of a diazo component of the benzene or naphthalene series or of the heterocyclic series, $R_1$ is hydrogen or $C_1$-$C_4$alkyl and $R_2$ is phenyl or substituted phenyl.

The radical D in formula (1) may carry the customary substituents of diazo components, including alkyl groups of 1 to 8, preferably 1 to 4, carbon atoms, typically methyl, ethyl, propyl, isopropyl, butyl, isobutyl, sec-butyl, tert-butyl, pentyl, hexyl heptyl or octyl; alkoxy groups of 1 to 8, preferably 1 to 4, carbon atoms, typically methoxy, ethoxy, propoxy, isopropoxy, butoxy; acylamino groups such as alkanoylamino groups of 2 to 8, preferably 2 to 4, carbon atoms, and alkoxycarbonylamino groups of 2 to 8 carbon atoms, typically acetylamino, propionylamino, methoxycarbonylamino, ethoxycarbonylamino; alkanoyl groups of 2 to 8, preferably 2 to 4, carbon atoms, typically acetyl, propionyl, butyryl or isobutyryl; amino; mono- or dialkylamino containing 1 to 8 carbon atoms in the alkyl moiety; carboxy; alkoxycarbonyl containing 1 to 8 carbon atoms in the alkoxy moiety; halogen, typically fluoro, bromo or, preferably, chloro; sulfo; arylazo groups such as the phenylazo and naphthylazo group; heterocyclic ring systems, including benzo[b]furyl, benzo[b]thiophenyl, indolyl, benzoxazolyl, benzothiazolyl, benzimidazolyl or benzotriazolyl; while the phenyl and naphthyl radicals as well as the heterocyclic ring systems may be further substituted by the substituents cited above. The radical D in formula (1) is preferably the radical of a diazo component of the benzene series.

$R_1$ as $C_1$-$C_4$alkyl may be methyl, ethyl, propyl, isopropyl, butyl, sec-butyl, isobutyl or tert-butyl.

$R_2$ defined as phenyl in formula (1) is suitably an unsubstituted phenyl radical or a phenyl radical which is substituted by $C_1$-$C_8$alkyl, preferably $C_1$-$C_4$alkyl, typically methyl, ethyl, propyl, isopropyl, butyl, isobutyl, sec-butyl and tert-butyl; $C_1$-$C_4$alkoxy, typically methoxy, ethoxy, propoxy, isopropoxy, butoxy, isobutoxy and sec-butoxy; halogen, typically fluoro, chloro and bromo; $C_2$-$C_4$alkanoylamino, typically acetylamino and propionylamino; and sulfo.

Preferred dyes of formula (1) are those wherein $R_1$ is hydrogen.

Further preferred dyes of formula (1) are those wherein $R_2$ is phenyl or phenyl which is substituted by $C_1$-$C_4$alkyl, $C_1$-$C_4$alkoxy, $C_2$-$C_4$alkanoylamino, halogen or sulfo, preferably by $C_1$-$C_4$alkyl, $C_1$-$C_4$alkoxy or halogen.

The dyes of formula (1) preferably contain only one sulfo group.

Also preferred are dyes of formula (1), wherein D is a radical of formula

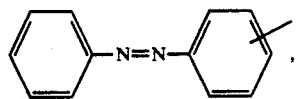

(2)

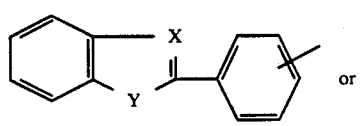

(3)

or

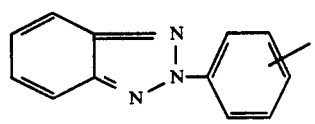

(4)

which radicals of formulae (2), (3) and (4) are unsubstituted or substituted as indicated for formula (1) and, in the radical of formula (3), X is a nitrogen atom or the —CH group and Y is an oxygen atom, a sulfur atom or the -NH group. The radicals D may preferably be substituted by $C_1$-$C_4$alkyl, $C_1$-$C_4$alkoxy, halogen, $C_2$-$C_4$alkanoylamino or sulfo, more particularly by $C_1$-$C_4$alkyl, $C_1$-$C_4$alkoxy, $C_2$-$C_4$alkanoylamino or halogen.

Particularly preferred dyes of formula (1) are those wherein $R_1$ is hydrogen, $R_2$ is phenyl or phenyl which is substituted by $C_1$-$C_4$alkyl, $C_1$-$C_4$alkoxy, $C_2$-$C_4$alkanoylamino, halogen or sulfo, and D is a radical of formula (2), (3) or (4), which radicals of formulae (2), (3) and (4) have the general and preferred meanings as indicated above.

Very particularly preferred dyes are those of formula

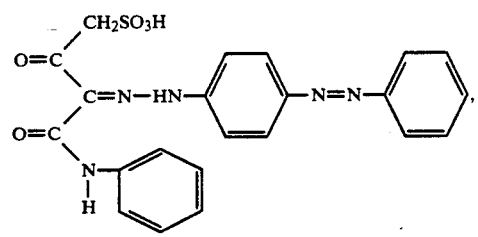

(5)

and dyes of formulae

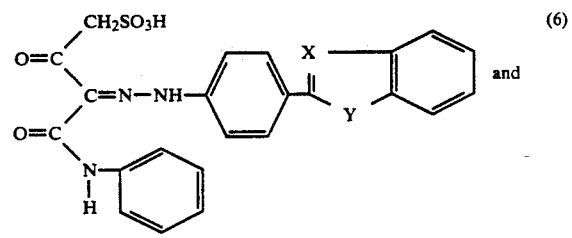

(6)

and

-continued

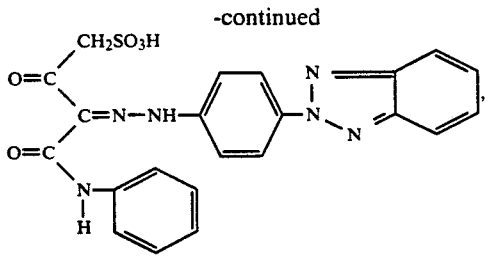

which dyes of formulae (5), (6) and (7) may be substituted by $C_1$-$C_4$alkyl, $C_1$-$C_4$alkoxy, $C_2$-$C_4$alkanoylamino, halogen or sulfo, preferably by $C_1$-$C_4$alkyl, $C_1$-$C_4$alkoxy, $C_2$-$C_4$alkanoylamino or halogen, and, in the dye of formula (6), X is a nitrogen atom or the —CH group and Y is an oxygen atom, a sulfur atom or the —NH group.

The invention further relates to a process for the preparation of the dyes of formula (1), which comprises diazotising an amine of formula $$D—NH_2 \quad (8)$$

and coupling the diazotised amine to a coupling component of formula

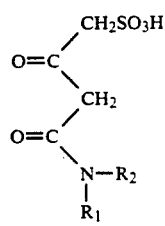

wherein D, $R_1$ and $R_2$ are as defined for formula (1).

The diazotisation of the amine of formula (8) is carried out in a manner which is known per se, typically with a nitrite, as with an alkali metal nitrite such as sodium nitrite, in a mineral acid medium, conveniently in hydrochloric acid, in the temperature range from -5° to 30° C., preferably from 0° to 10° C.

The coupling of the diazotised amine to the coupling component of formula (9) is carried out in a manner which is known per se, in the acid, neutral or alkaline pH range and in the temperature range from typically 0° to 30° C.

Exemplary of amines of formula (8) are 4-aminoazobenzene, 3-methoxy-4-aminoazobenzene, 2-(4'-aminophenyl)benzothiazole, 2-(4'-aminophenyl)-6-methylbenzothiazole, 2-(4'-aminophenyl)benzoxazole, 2-(4'-aminophenyl)-5-methylbenzoxazole, 2-(4'-aminophenyl)benzimidazole, 2-(4'-aminophenyl)benzotriazole, 2-(4'-aminophenyl)benzo[b]furan and 2-(4'-aminophenyl)-5-methylbenzo[b]furan.

Exemplary of coupling components of formula (9) are compounds of formula (9), wherein $R_1$ is hydrogen and $R_2$ is phenyl, 2- or 4-methoxyphenyl, 2,4-dimethoxyphenyl, 2,4-diethoxyphenyl, 2,4-dimethoxy-5-chlorophenyl, 2,5-dimethoxy-4-chlorophenyl, 2- or 4-chlorophenyl, 2,4-dichlorophenyl or 2-methyl-3-chlorophenyl.

Preferred embodiments of the inventive process comprise using a coupling component of formula (9), wherein $R_1$ is hydrogen;

using a coupling component of formula (9), wherein $R_2$ is phenyl or phenyl which is substituted by $C_1$-$C_4$alkyl, $C_1$-$C_4$alkoxy, $C_2$-$C_4$alkanoylamino, halogen or sulfo, preferably by $C_1$-$C_4$alkyl, $C_1$-$C_4$alkoxy or halogen;

using an amine of formula (8), wherein D is a radical of formula (2), (3) or (4), which radicals of formulae (2), (3) and (4) may be substituted by $C_1$-$C_4$alkyl, $C_1$-$C_4$alkoxy, $C_2$-$C_4$alkanoylamino, halogen or sulfo, preferably by $C_1$-$C_4$alkyl, $C_1$-$C_4$alkoxy, $C_2$-$C_4$alkanoylamino or halogen, and, in the radical of formula (3), X and Y are as defined for formula (3);

using an amine of formula (8) and a coupling component of formula (9) which together contain only one sulfo group.

A particularly preferred embodiment of the inventive process comprises diazotising an amine of formula

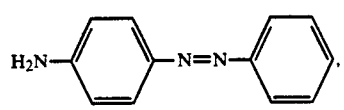

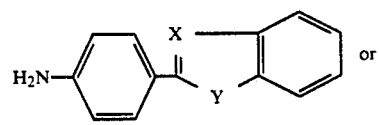

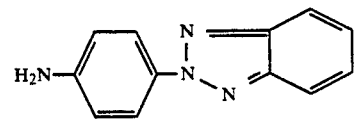

and coupling the diaziotised amine to a coupling component of formula

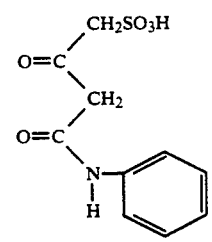

wherein X and Y in the amine of formula (11) are as defined for formula (3), and the amines of formulae (10), (11) and (12) and the coupling component of formula (13) may be substituted by $C_1$-$C_4$alkyl, $C_1$-$C_4$alkoxy, $C_2$-$C_4$alkanoylamino, halogen or sulfo, preferably by $C_1$-$C_4$alkyl, $C_1$-$C_4$alkoxy, $C_2$-$C_4$alkanoylamino or halogen.

The amines of formula (8) are known or they can be prepared by methods analogous to those for obtaining known compounds.

The coupling components of formula (9) are novel and constitute a further object of the present invention.

The invention accordingly also relates to compounds of formula (9), wherein $R_1$ and $R_2$ are as defined for formula (1).

Compounds of formula (9), wherein $R_1$ is hydrogen, are preferred.

More preferred are compounds of formula (9), wherein $R_2$ is phenyl or phenyl which is substituted by $C_1$-$C_4$alkyl, $C_1$-$C_4$alkoxy, $C_2$-$C_4$alkanoylamino, halogen or sulfo, preferably by $C_1$-$C_4$alkyl, $C_1$-$C_4$alkoxy or halogen.

Particularly preferred compounds of formula (9) are those wherein $R_1$ is hydrogen and $R_2$ is phenyl or phenyl which is substituted by $C_1$-$C_4$alkyl, $C_1$-$C_4$alkoxy or halogen.

The compounds of formula (9) are prepared by reacting a compound of formula

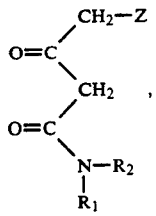
(14)

wherein $R_1$ and $R_2$ are as defined for formula (1) and Z is an anionic leaving group, by replacing the radical Z with a sulfo group to give the compound of formula (9).

A suitable anionic group Z may be halogen, typically fluoro, bromo or, preferably, chloro.

The sulfo group is introduced into the compound of formula (9) by replacing the radical Z with a sulfo group, conveniently with an alkali metal sulfite, preferably sodium sulfite, in a solvent such as water or a mixture of water and ethanol, in the temperature range from 30° to 100° C., preferably from 50° to 70° C., in the acid, neutral or alkaline pH range.

The compounds of formula (14) are known or they can be prepared by methods analogous to those for obtaining known compounds.

The dyes of formula (1) and the compounds of formula (9) are obtained either in the form of the free acid or, preferably, of salts thereof.

Suitable salts are typically the alkali or ammonium salts or salts of an organic amine. Exemplary of such salts are the sodium, lithium, potassium or ammonium salts or the salt of mono-, di- or triethanolamine.

The novel dyes of formula (1) are suitable for dyeing and printing nitrogen-containing or hydroxyl group containing fibre materials, paper or leather, including textile materials made from cellulose, silk and natural and synthetic polyamide fibre materials, by methods which are known per se. The dyes of formula (1) may be used for dyeing and printing in conventional, optionally preformulated form. The dyeings obtained have good allround fastness properties, especially good fastness to rubbing, wet rubbing and light. In addition, the novel dyes are readily water-soluble. The novel dyes also have good build-up and can be readily combined with other dyes. They are also suitable for dyeing or printing natural and synthetic polyamide fibre material by the trichromatic process using dye mixtures which contain a dye of formula (1) together with a red-dyeing dye and a blue-dyeing dye. The textile material may be in any form of presentation, typically as fibres, yarn, woven or knitted goods.

In the following Examples parts are by weight. The relationship between parts by weight and parts by volume is the same as that between the gram and the cubic centimetre.

EXAMPLE 1

88 parts of diketene are dissolved in 660 parts of carbon tetrachloride and the solution is cooled to a temperature of −20° C. At this temperature 71 parts of chlorine gas are introduced over 1 hour. The batch is stirred for 90 minutes at −20° C. and the temperature is raised to 0°-5° C. A separate solution of 126 parts of p-anisidine and 102 parts of triethylamine in 1300 parts of toluene is prepared. This solution is cooled to a temperature of 0°-5° C. and then stirred into the initially prepared solution over 45 minutes, while keeping the temperature below 5° C. Stirring is then continued for 6 hours at 0°-5° C. The product is collected by suction filtration, washed thoroughly with 900 parts of toluene and then with 1000 parts of water and dried, giving 218 parts of a beige powder which corresponds to the compound of formula

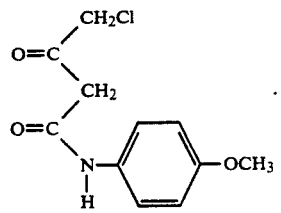
(101)

48 parts of the above compound of formula (101) are added to a mixture of 400 parts of water and 800 parts of ethanol and the temperature is raised to 60° C. A solution of 26 parts of sodium sulfite in 200 parts of water is added over 10 minutes and the reaction mixture is stirred for 1 hour, while keeping the temperature at 60° C. The solvent is removed by freeze drying, giving 74 parts of a colourless powder which, in the form of the free acid, corresponds to the compound of formula

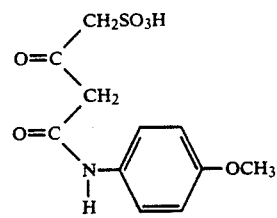
(102)

and has a purity of 83%.

EXAMPLES 2 to 11

The procedure of Example 1 is repeated, replacing 126 parts of p-anisidine with an equimolar amount of one of the anilino compounds listed in column 2 of Table 1, giving the acetoacetanilides listed in column 3 of the table.

TABLE 1

| Ex. | Anilino compound | Acetoacetanilide |
|---|---|---|
| 2 | aniline | (structure: $CH_2SO_3H$, $O=C$, $CH_2$, $O=C$, $N-C_6H_5$, H) |

TABLE 1-continued

| Ex. | Anilino compound | Acetoacetanilide |
|---|---|---|
| 3 | o-anisidine | (structure: CH₂SO₃H–C(=O)–CH₂–C(=O)–NH–C₆H₄(o-OCH₃)) |
| 4 | p-chloroaniline | (structure: CH₂SO₃H–C(=O)–CH₂–C(=O)–NH–C₆H₄(p-Cl)) |
| 5 | o-chloroaniline | (structure: CH₂SO₃H–C(=O)–CH₂–C(=O)–NH–C₆H₄(o-Cl)) |
| 6 | 2,4-dimethoxyaniline | (structure: CH₂SO₃H–C(=O)–CH₂–C(=O)–NH–C₆H₃(2-OCH₃, 4-OCH₃)) |
| 7 | 2,4-dimethoxy-5-chloro-aniline | (structure: CH₂SO₃H–C(=O)–CH₂–C(=O)–NH–C₆H₂(2-OCH₃, 4-OCH₃, 5-Cl)) |
| 8 | 2-methyl-3-chloroaniline | (structure: CH₂SO₃H–C(=O)–CH₂–C(=O)–NH–C₆H₃(2-CH₃, 3-Cl)) |
| 9 | 2,5-dimethoxy-4-chloro-aniline | (structure: CH₂SO₃H–C(=O)–CH₂–C(=O)–NH–C₆H₂(2-OCH₃, 5-OCH₃, 4-Cl)) |
| 10 | 2,4-dichloroaniline | (structure: CH₂SO₃H–C(=O)–CH₂–C(=O)–NH–C₆H₃(2-Cl, 4-Cl)) |
| 11 | 2,4-diethoxyaniline | (structure: CH₂SO₃H–C(=O)–CH₂–C(=O)–NH–C₆H₃(2-OC₂H₅, 4-OC₂H₅)) |

EXAMPLE 12

39 parts of 4-aminoazobenzene are stirred in 600 parts of water and the mixture is cooled by addition of 400 parts of ice. Then 47 parts of hydrochloric acid (32%) are added and the temperature is kept at 0°–5° C. by external cooling. A solution of 15 parts of sodium nitrite in 50 parts of water are then added over 10 minutes, while keeping the temperature below 5° C. The reddish brown solution is stirred for 2 hours at 0°–5° C., and then any excess nitrite is destroyed with urea. Meanwhile a separate solution of 82 parts of the compound of formula (102) according to Example 1 (83%) and 91 parts of sodium acetate in 600 parts of water is prepared and cooled to a temperature of 0°–5° C. The above described solution of the diazonium salt is then stirred into this separately prepared solution over 20 minutes, while keeping the temperature below 5° C. The orange suspension is stirred for 5 hours at 0°–5° C., then for another 15 hours at room temperature, and the product is collected by suction filtration. The filter product is dried, giving 97 parts of an orange powder which, in the form of the free acid, corresponds to the dye of formula

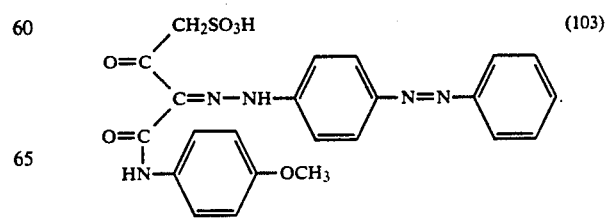

(103)

The dye of formula (103) dyes natural and synthetic polyamide fibre material in a yellow shade.

EXAMPLES 13 to 34

The procedure of Example 12 is repeated, replacing 82 parts of the compound of formula (102) according to Example 1 with an equimolar amount of one of the coupling components indicated in column 2 of Table 2, and replacing 39 parts of 4-aminoazobenzene with an equimolar amount of one of the amines listed in column 3 of the table, giving analogous dyes which dye natural and synthetic polyamide fibre material in the shades indicated in column 4.

TABLE 2

| Ex. | Coupling component | Amine | Shade on polyamide |
|---|---|---|---|
| 13 | $O=C(CH_2SO_3H)-CH_2-C(=O)-NH-C_6H_5$ | $C_6H_5-N=N-C_6H_4-NH_2$ | yellow |
| 14 | $O=C(CH_2SO_3H)-CH_2-C(=O)-NH-(2-OCH_3)C_6H_4$ | $C_6H_5-N=N-C_6H_4-NH_2$ | yellow |
| 15 | $O=C(CH_2SO_3H)-CH_2-C(=O)-NH-(4-Cl)C_6H_4$ | $C_6H_5-N=N-C_6H_4-NH_2$ | yellow |
| 16 | $O=C(CH_2SO_3H)-CH_2-C(=O)-NH-(2-Cl)C_6H_4$ | $C_6H_5-N=N-C_6H_4-NH_2$ | yellow |
| 17 | $O=C(CH_2SO_3H)-CH_2-C(=O)-NH-(2-OCH_3, 4-OCH_3)C_6H_3$ | $C_6H_5-N=N-C_6H_4-NH_2$ | yellow |
| 18 | $O=C(CH_2SO_3H)-CH_2-C(=O)-NH-(2-OCH_3, 4-Cl, 5-OCH_3)C_6H_2$ | $C_6H_5-N=N-C_6H_4-NH_2$ | yellow |

TABLE 2-continued

| Ex. | Coupling component | Amine | Shade on polyamide |
|---|---|---|---|
| 19 | CH₂SO₃H–CO–CH₂–CO–NH–(2-CH₃, 3-Cl-phenyl) | C₆H₅–N=N–C₆H₄–NH₂ | yellow |
| 20 | CH₂SO₃H–CO–CH₂–CO–NH–(2,5-dimethoxy-4-chlorophenyl) | C₆H₅–N=N–C₆H₄–NH₂ | yellow |
| 21 | CH₂SO₃H–CO–CH₂–CO–NH–(2,4-dichlorophenyl) | C₆H₅–N=N–C₆H₄–NH₂ | yellow |
| 22 | CH₂SO₃H–CO–CH₂–CO–NH–(4-OCH₃-phenyl) | C₆H₅–N=N–(3-OCH₃, 4-NH₂-phenyl) | yellow orange |
| 23 | CH₂SO₃H–CO–CH₂–CO–NH–C₆H₅ | 4-methyl-2-(4-aminophenyl)benzothiazole | greenish yellow |
| 24 | CH₂SO₃H–CO–CH₂–CO–NH–(4-OCH₃-phenyl) | 4-methyl-2-(4-aminophenyl)benzothiazole | greenish yellow |
| 25 | CH₂SO₃H–CO–CH₂–CO–NH–(4-OCH₃-phenyl) | 5-methyl-2-(4-aminophenyl)benzoxazole | greenish yellow |

TABLE 2-continued

| Ex. | Coupling component | Amine | Shade on polyamide |
|---|---|---|---|
| 26 | Coupling component with CH₂SO₃H, C=O, CH₂, C=O, NH, phenyl-OCH₃ | 2-(4-aminophenyl)benzimidazole | greenish yellow |
| 27 | Coupling component with CH₂SO₃H, C=O, CH₂, C=O, NH, phenyl-OCH₃ | 2-(4-aminophenyl)-2H-benzotriazole | greenish yellow |
| 28 | Coupling component with CH₂SO₃H, C=O, CH₂, C=O, NH, phenyl-OCH₃ | 2-(4-aminophenyl)-5-methylbenzofuran | greenish yellow |
| 29 | Coupling component with CH₂SO₃H, C=O, CH₂, C=O, NH, phenyl-OCH₃ | 2,5-dimethoxy-4-(phenylazo)aniline | orange |
| 30 | Coupling component with CH₂SO₃H, C=O, CH₂, C=O, NH, phenyl with OC₂H₅ and H₅C₂O | 4-(phenylazo)aniline | yellow orange |
| 31 | Coupling component with CH₂SO₃H, C=O, CH₂, C=O, NH, phenyl with OC₂H₅ and H₅C₂O | 2-methoxy-4-(phenylazo)aniline | yellow |

TABLE 2-continued

| Ex. | Coupling component | Amine | Shade on polyamide |
| --- | --- | --- | --- |
| 32 | ![structure] | ![structure] | yellow orange |
| 33 | ![structure] | ![structure] | yellow orange |
| 34 | ![structure] | ![structure] | yellow orange |

Dyeing procedure I 10 parts of polyamide 66 material are dyed in 500 parts of an aqueous liquor which contains 2 g/l of ammonium acetate and is adjusted to pH 5 with acetic acid. The amount of dye of formula (103) according to Example 12 is 0.7%, based on the weight of the material. The dyeing time at a temperature of 98° C. is from 30 to 90 minutes. The dyed polyamide 66 material is then removed from the dyebath and washed and dried in conventional manner.

The polyamide 66 material is dyed in a pure yellow shade of good allround fastness properties.

Dyeing procedure II 10 parts of polyamide 66 material are dyed in 500 parts of an aqueous liquor which contains 1 g/l of monosodium phosphate and is adjusted to pH 6 with disodium phosphate. The amount of dye of formula (103) according to Example 12 is 1%, based on the weight of the material. The dyeing time is 30 to 90 minutes at a temperature of 98° C. The dyed polyamide 66 material is then removed from the dyebath and washed and dried in conventional manner.

The polyamide 66 material is dyed in a pure yellow shade of good allround fastness properties.

Dyeing procedure III 10 parts of woollen piece goods are dyed in 500 parts of an aqueous liquor. Based on the weight of the material, the liquor contains 0.45% of dye of formula (103) according to Example 12, 5% of calc. Glauber's salt and 2% of 80% acetic acid. The dyeing time is 30–60 minutes at a temperature of 98° C. The woollen fabric is washed and dried in conventional manner and is dyed in a yellow shade of good allround fastness properties.

What is claimed is:

1. A dye of the formula

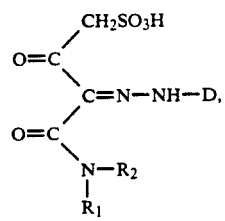

(1)

wherein D is the radical of a diazo component of the benzene or naphthalene series or of the heterocyclic series, $R_1$ is hydrogen or $C_1$–$C_4$alkyl and $R_2$ is unsubstituted phenyl or phenyl which is substituted by $C_1$–$C_4$alkyl, $C_1$–$C_4$alkoxy, $C_2$–$C_4$alkanoylamino or halogen, and wherein the dye of formula (1) contains only one sulfo group.

2. A dye according to claim 1, wherein $R_1$ is hydrogen.

3. A dye according to claim 1, wherein D is a radical of the formula

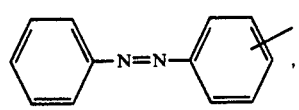

(2)

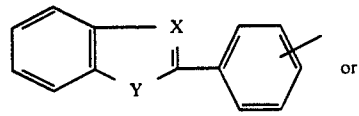

or (3)

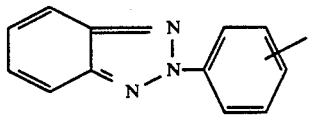

which radicals of formulae (2), (3) and (4) are unsubstituted or substituted by $C_1$-$C_4$alkyl, $C_1$-$C_4$alkoxy, $C_2$-$C_4$alkanoylamino or halogen and, in the radical of formula (3), X is a nitrogen atom or the —CH group and Y is an oxygen atom, a sulfur atom or the —NH group.

4. A dye according to claim 1 of formula

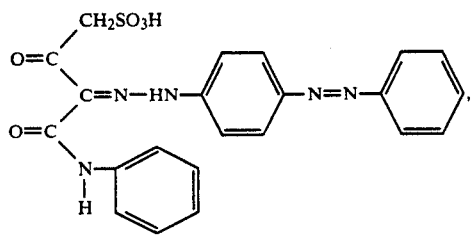

which dye may be substituted by $C_1$-$C_4$alkyl, $C_1$-$C_4$alkoxy, $C_2$-$C_4$alkanoylamino or halogen.

5. A dye according to claim 1 of formula

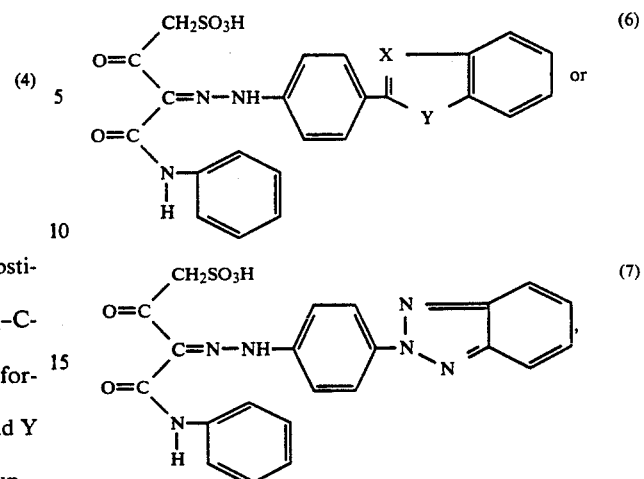

which dye of formula (6) or (7) may be substituted by $C_1$-$C_4$alkyl, $C_1$-$C_4$alkoxy, $C_2$-$C_4$alkanoylamino or halogen, and, in the dye of formula (6), X is a nitrogen atom or the —CH group and Y is an oxygen atom, a sulfur atom or the —NH group.

6. A compound of the formula

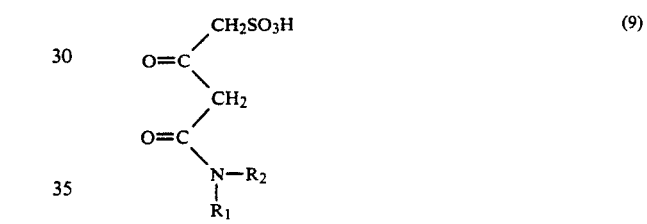

wherein $R_1$ is hydrogen or $C_1$-$C_4$alkyl and $R_2$ is unsubstituted phenyl or phenyl which is substituted by $C_1$-$C_4$alkyl, $C_1$-$C_4$alkoxy, $C_2$-$C_4$alkanoylamino or halogen.

* * * * *